US009829446B1

(12) United States Patent
Solazzi et al.

(10) Patent No.: US 9,829,446 B1
(45) Date of Patent: *Nov. 28, 2017

(54) SAMPLE CUP AND METHOD FOR MOUNTING A THIN FILM OF MATERIAL ACROSS A SAMPLE CUP

(71) Applicant: CHEMPLEX INDUSTRIES, INC., Palm City, FL (US)

(72) Inventors: Michael C. Solazzi, Palm City, FL (US); Monte J. Solazzi, Palm City, FL (US)

(73) Assignee: CHEMPLEX INDUSTRIES, INC., Palm City, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/783,463

(22) Filed: Mar. 4, 2013

Related U.S. Application Data

(60) Provisional application No. 61/606,578, filed on Mar. 5, 2012.

(51) Int. Cl.
*B01L 3/00* (2006.01)
*G01N 23/20* (2006.01)

(52) U.S. Cl.
CPC .............................. *G01N 23/20025* (2013.01)

(58) Field of Classification Search
CPC .. G01N 21/64; G01N 23/223; G01N 23/2204; B01L 3/508
USPC ..................... 378/47; 422/547, 557; 436/172
See application file for complete search history.

(56) References Cited

U.S. PATENT DOCUMENTS

| 2,127,397 | A | 3/1938 | Freedlander |
| 2,144,255 | A | 1/1939 | Carpenter |
| 4,037,109 | A | 7/1977 | Hosokawa et al. |
| 4,046,138 | A | 9/1977 | Libman et al. |
| 4,148,732 | A | 4/1979 | Burrow et al. |
| 4,184,360 | A | 1/1980 | Vadnay et al. |
| 4,256,474 | A | 3/1981 | Berger, Jr. et al. |
| 4,301,010 | A | 11/1981 | Eddleman et al. |
| 4,346,299 | A | 8/1982 | Mitteldorf |
| 4,362,047 | A | 12/1982 | vonReis et al. |
| 4,402,909 | A | 9/1983 | Solazzi |
| 4,409,854 | A | 10/1983 | Solazzi |
| 4,448,311 | A | 5/1984 | Houser |

(Continued)

FOREIGN PATENT DOCUMENTS

DE          1222425          8/1966

*Primary Examiner* — Jill Warden
*Assistant Examiner* — Dwayne K Handy
(74) *Attorney, Agent, or Firm* — Keene IP Law, LLC

(57) ABSTRACT

A sample analysis cup, sample cup assembly, and method is provided including a cell body with an open top end including an outer top wall and an inner top wall, each extending axially and positioned in concentric relationship; a bottom wall extending from the outer top wall to the inner top wall, the bottom wall and the inner and outer top walls defining an internal reservoir therebetween; a transverse wall extending a selected distance from the inner top wall, the transverse wall partially closing the open top end; an open bottom end including an outer bottom wall and an inner bottom wall, each extending axially and positioned in concentric relationship, the outer and inner bottom walls defining an internal channel therebetween; and a hollow chamber defined between the open top end and the open bottom end.

20 Claims, 6 Drawing Sheets

(56) References Cited

U.S. PATENT DOCUMENTS

| | | | |
|---|---|---|---|
| 4,575,869 | A | 3/1986 | Torrisi |
| 4,587,666 | A | 5/1986 | Torrisi |
| 4,643,033 | A | 2/1987 | Solazzi |
| 4,665,759 | A | 5/1987 | Solazzi |
| 4,698,210 | A | 10/1987 | Solazzi |
| 4,961,916 | A | 10/1990 | Lesage et al. |
| 4,974,244 | A | 11/1990 | Torrisi |
| 4,982,615 | A | 1/1991 | Sultan et al. |
| 5,323,441 | A | 6/1994 | Torrisi et al. |
| 5,351,281 | A | 9/1994 | Torrisi |
| 5,451,375 | A | 9/1995 | Solazzi |
| 5,454,020 | A | 9/1995 | Solazzi |
| RE35,506 | E | 5/1997 | Solazzi |
| 5,630,989 | A | 5/1997 | Solazzi |
| 5,703,927 | A | 12/1997 | Torrisi |
| 6,009,766 | A | 1/2000 | Solazzi |
| 6,428,751 | B1 | 8/2002 | Solazzi |
| 7,722,821 | B2 | 5/2010 | Solazzi |
| 7,981,380 | B2 | 7/2011 | Solazzi |
| 8,043,862 | B2 | 10/2011 | Solazzi |
| 8,404,197 | B2 | 3/2013 | Solazzi |
| 2009/0141867 | A1* | 6/2009 | Burdett et al. ............... 378/208 |

* cited by examiner

SAMPLE CUP AND METHOD FOR MOUNTING A THIN FILM OF MATERIAL ACROSS A SAMPLE CUP

RELATED APPLICATION

This application claims the benefit of U.S. Provisional Patent Application No. 61/606,578, filed on Mar. 5, 2012, the entire disclosure of which is hereby incorporated by reference herein.

FIELD OF THE INVENTION

The invention relates generally to sample analysis cups, and more particularly, to sample analysis cups used in spectrochemical analysis.

BACKGROUND OF THE INVENTION

Spectroscopy is an analytical science where the characteristics or properties of a sample substance are determined based on the spectra of energy that the sample absorbs or emits. Technological advancements in both wavelength-dispersive (WD-XRF) and energy-dispersive (ED-XRF) X-ray fluorescence instrumentation enable the spectroscopic analysis of many types of sample materials, including liquid, solid, and powdered specimens.

Sample analysis cups are used with spectroscopic instrumentation to retain the sample substances during analysis. The sample substances may be disposed in a central chamber of a sample cup. A thin film of material may be disposed across an open end of a cup to retain a sample substance within the chamber and to provide a sample surface plane which is exposed to an excitation source, such as an X-ray beam, laser diode or other energy sources. The sample substance contained in the cup is subjected to analysis when energy beams impinge upon the sample surface plane. It is essential for the surface of the thin film of material, which covers an open end of the cell body, to remain planar and taut during analysis in order to produce reliable, accurate, and precise data.

With the spectrochemical analysis of specimens that exhibit high abrogation in air, a sample cup containing a specimen may be placed within a vacuum or pressurized inert gas environment. Under vacuum conditions where pressure equalization is not implemented, the thin film of material will distend outwardly due to the differential in pressures between the area within the sample cup and the environment surrounding the sample cup, which places portions of the thin film of material closer to the source of excitation. The variation and decrease in distance from the sample surface plane to the source of excitation alters the absorption and emission of radiation from the sample specimen and the intensity of radiation impinging upon the specimen. Consequently, erroneous qualitative and quantitative data may be produced.

In applications requiring a pressurized inert gaseous environment, where pressure is greater on the outside of the sample cup than inside the sample cup, the thin film of material distends into the hollow of the sample cup providing a concave sample surface, thereby increasing the distance between the sample surface plane and the excitation source, also resulting in erroneous analytical data.

To equalize the pressure between the inside and outside of the sample cups, and to eliminate distension of the sample surface plane, some sample cups are provided with a venting means, or may include a vent hole in the top or cap of an assembled cup. The venting means may be activated or punctured to provide pressure equalization between the inside and outside of the cup. Other sample cups may include a main cell body with a double open-ended cup, which, upon assembly with a thin film, allows for continuous venting during analysis.

In addition to the problem of distention, the sample substance contained in a sample cup may escape or exude from the central chamber during analysis onto the analysis chamber, an X-ray tube, an X-ray detector, or other delicate electronic components of the instrumentation, causing damage thereto. In addition, the exuded sample substance may cause contamination issues, costly cleanups, and non-productive down time.

There remains a need for sample cups that provide a planar sample surface plane while substantially eliminating the possibility of any sample exuding from the cup during analysis, and the subsequent damage and contamination to the instrumentation.

SUMMARY OF THE INVENTION

According to an aspect of the invention, a sample analysis cup includes a a cell body, including: an open top end including an outer top wall and an inner top wall, each of the walls extending axially and positioned in concentric relationship; a bottom wall extending from the outer top wall to the inner top wall, the bottom wall and the inner and outer top walls defining an internal reservoir therebetween; a transverse wall extending a selected distance from the inner top wall, the transverse wall partially closing the open top end; an open bottom end including an outer bottom wall and an inner bottom wall, each of the walls extending axially and positioned in concentric relationship, the outer and inner bottom walls defining an internal channel therebetween; and a hollow chamber defined between the open top end and the open bottom end is provided.

According to an aspect of the invention, a sample cup assembly including a cell body, including: an open top end including an outer top wall with and an inner top wall, each of the walls extending axially and positioned in concentric relationship; a bottom wall extending from the outer top wall to the inner top wall, the bottom wall and the inner and outer walls defining an internal reservoir therebetween; a transverse wall extending a selected distance from the inner top wall, the transverse wall partially closing the open top end; an open bottom end including an outer bottom wall and an inner bottom wall, each of the walls extending axially and positioned in concentric relationship, the outer and inner bottom walls defining an internal channel therebetween; and a hollow analysis chamber defined between the open top end and the open bottom end; a thin film of material; an annular ring member configured for insertion into the internal channel for retaining the thin film of material; and a rotatable cap configured for placement on the open top end is also provided.

According to another aspect of the invention, a method for mounting a thin film of material across an open end of a sample cup includes the steps of: providing a cell body including: an open top end including an outer top wall and an inner top wall, each of the walls extending axially and positioned in concentric relationship; a bottom wall extending from the outer top wall to the inner top wall, the bottom wall and the outer and inner top walls defining an internal reservoir therebetween; a transverse wall extending a selected distance from the inner top wall, the transverse wall partially closing the open top end; an open bottom end including an outer bottom wall and an inner bottom wall, each of the walls extending axially and positioned in concentric relationship, the outer and inner bottom walls defining an internal channel therebetween; and a hollow chamber defined between the open top end and the open bottom end; disposing a thin film of material across the open bottom end; inserting an annular ring member into the internal channel; and disposing a rotatable cap on the partially closed open top end is also provided.

BRIEF DESCRIPTION OF THE DRAWINGS

Throughout the drawings, like reference numerals are used to indicate common features of the described devices.

The above-identified drawing figures set forth several of the embodiments of the invention. Other embodiments are also contemplated, as disclosed herein. The disclosure represents the invention, but is not limited thereby, as it should be understood that numerous other modifications and embodiments may be devised by those skilled in the art which fall within the scope and spirit of the invention as claimed.

DETAILED DESCRIPTION OF THE INVENTION

As used herein, the terms "comprises", "comprising", "includes", "including", "has", "having", or any other variation thereof, are intended to cover non-exclusive inclusions. For example, a process, method, article or apparatus that comprises a list of elements is not necessarily limited to only those elements but may include other elements not expressly listed or inherent to such process, method, article, or apparatus. In addition, unless expressly stated to the contrary, the term "of" refers to an inclusive "or" and not to an exclusive "or". For example, a condition A or B is satisfied by any one of the following: A is true (or present) and B is false (or not present); A is false (or not present) and B is true (or present); and both A and B are true (or present).

The terms "a" or "an" as used herein are to describe elements and components of the invention. This is done for convenience to the reader and to provide a general sense of the invention. The use of these terms in the description herein should be read and understood to include one or at least one. In addition, the singular also includes the plural unless indicated to the contrary. For example, reference to a device containing "an element" includes one or more elements. As used in this specification and the appended claims, the term "or" is generally employed in its sense including "and/or" unless the content clearly dictates otherwise.

All numeric values are herein assumed to be modified by the term "about," whether or not explicitly indicated. The term "about" generally refers to a range of numbers that one of skill in the art would consider equivalent to the recited value (i.e., having the same function or result). In any instances, the terms "about" may include numbers that are rounded to the nearest significant figure.

Figure 1:
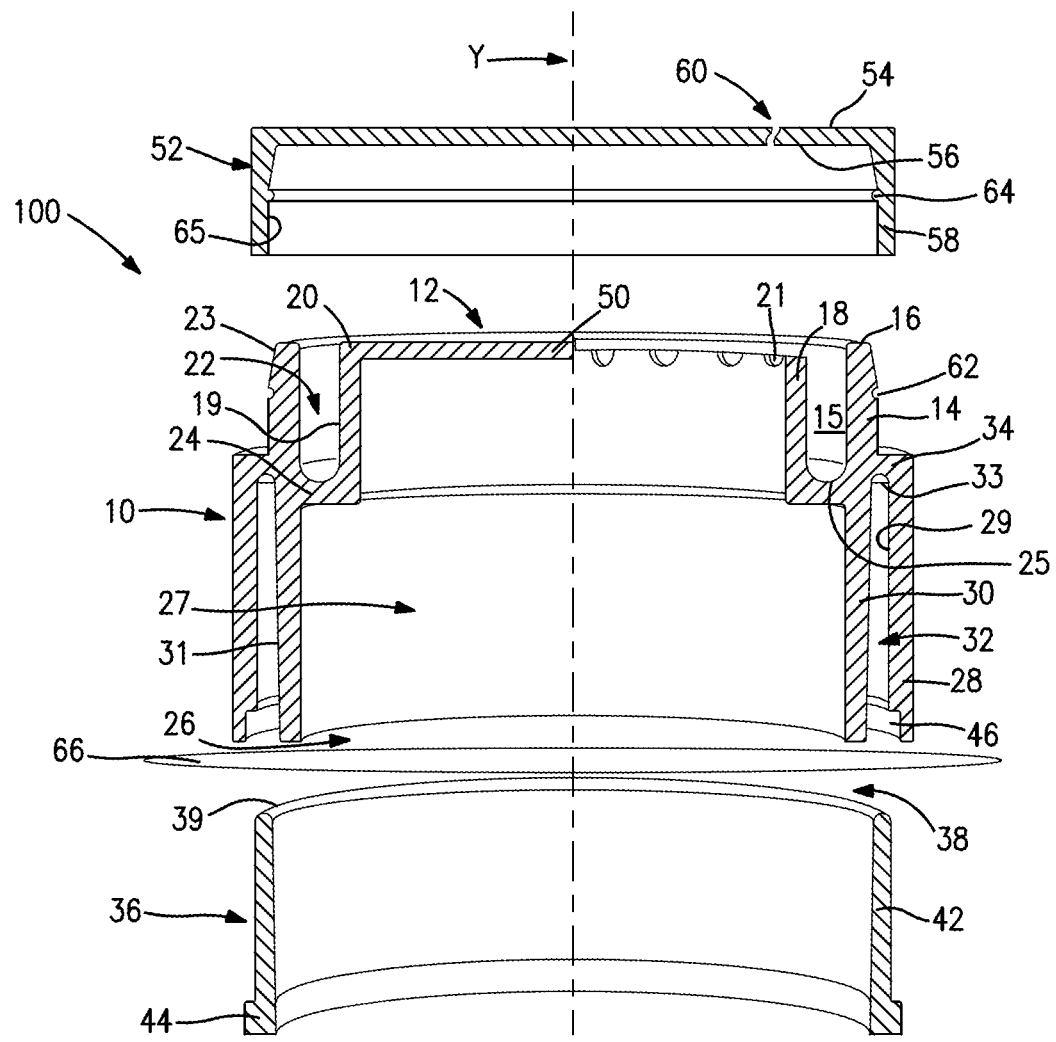
FIG. 1 is an exploded view of the sample cup and a sample cup assembly according to an aspect of the invention.

Referring to FIG. 1, according to an aspect of the invention, a sample cup assembly 100 includes a generally open-ended and cylindrical tiered cell body 10. As illustrated in FIG. 1, toward the upper portion of the cell body 10, adjacent the open top end 12 is an annular outer top wall 14 with an outer top planar edge 16 and an annular inner top wall 18 with an inner top edge 20. The inner top edge 20 of annular inner top wall 18 includes a planar portion 50 disposed thereon. Inner top edge 20 also includes a series of semi-spherical channels 21 disposed along a portion of the inner edge 20 that extend from the inner surface 17 of wall 18 through to the outer surface 19. Parallel outer top and inner top walls 14 and 18 extend axially and are positioned in concentric relationship about central axis Y.

An annular internal overflow reservoir 22 is defined in the space between the inner surface 15 of outer top wall 14, the outer surface 19 of inner top wall 18, and the rounded, concave upper surface 25 of transverse horizontal wall 24. As illustrated in FIG. 1, the overflow reservoir has a U-shaped cross-section. It should be understood that the upper surface of transverse horizontal wall 24 may also be flat or planar, with the resulting cross-section being hemi-rectangular.

Figure 3:
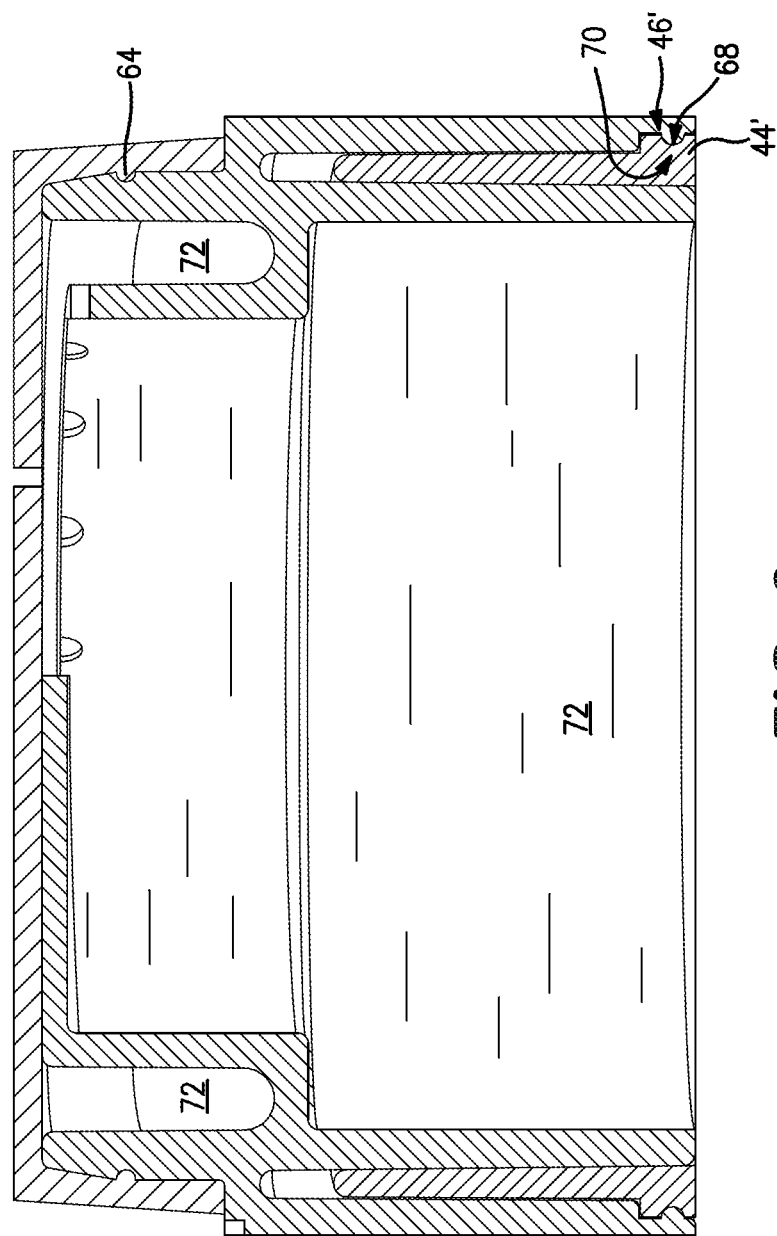
FIG. 3 is a cross-sectional view illustrating the sample cup according to an aspect of the invention.

During analysis, thermally-sensitive sample materials may expand in volume due to excitation from the energy beam. Internal overflow reservoir 22 is configured for receiving the overflow of a thermally-sensitive liquid sample 72 from the analysis chamber 27 (FIG. 3). According to an aspect of the invention, the inner top edge 20 of the inner top wall 18 is positioned a selected distance below the outer top edge 16 of outer top wall 14. According to another aspect of the invention, the inner top edge 20 is at the same level and planar with the outer top edge 16. Regardless of the height of the inner top edge 20, any expanded sample overflows from the analysis chamber through the series of channels 21 and into the internal reservoir 22, and is retained in the internal reservoir 22 to prevent the expanded sample from escaping from the cell assembly and causing possible damage to the instrumentation and the concomitant and time-consuming decontamination clean-ups associated therewith.

Still referring to FIG. 1, the lower portion of cell body 10 includes an open bottom end 26 with an outer bottom wall 28 and an inner bottom wall 30. Parallel outer and inner bottom walls 28 and 30 extend axially and are positioned in concentric relationship about central axis Y. The inner bottom wall 30 adjoins the outer top wall 14. An internal receiving channel 32 is defined in the annular space between the inner surface 29 of outer bottom wall 28, the outer surface 31 of inner bottom wall 28, and the lower surface 33 of outer transverse horizontal wall 34.

Still referring to FIG. 1, a substantially cylindrical, and two-tiered hollow analysis chamber 27, defined in the space between the annular inner top wall 18, from the inner top edge 20 to the open bottom end 26, is configured for receiving a sample material 72 and retaining the sample material before, during, and after spectrochemical analysis.

As further illustrated in FIG. 1, an annular collar 36, configured for insertion into the internal receiving channel 32, includes an open top end 38, an open bottom end 40, and a substantially cylindrical wall 42. Annular collar 36 may include an external peripheral flange 44 disposed about the outer periphery of the open bottom end 40. The edge 39 of the open top end 38 may be rounded to avoid tearing a thin film of material upon assembly, as will be described hereinafter.

Figure 2:
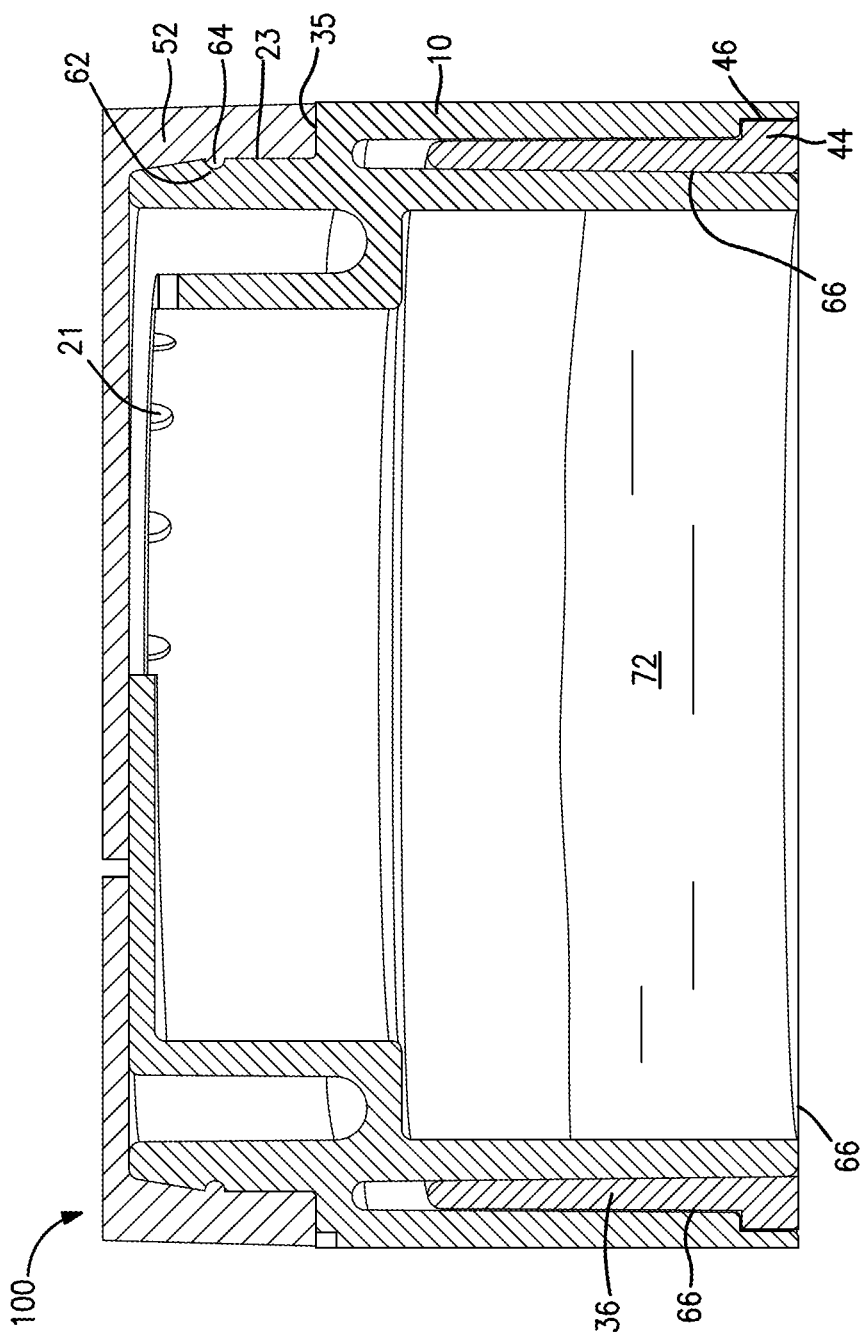
FIG. 2 is a cross-sectional view illustrating the sample cup according to an aspect of the invention.

When external peripheral flange 44 is present on the annular collar 36, the inner surface 29 of the outer bottom wall 28 of cell body 10 includes an internal peripheral recess 46 having a shape complementary to the external peripheral flange 44. According to an aspect of the invention, the external peripheral flange 44 and the internal peripheral recess 46 may be rectangular or square in cross-section as illustrated in FIGS. 1 and 2, or external peripheral flange 44' may be configured with an indent 70 and the internal peripheral recess 46' with a bead 68 as illustrated in FIG. 3.

Figure 4:
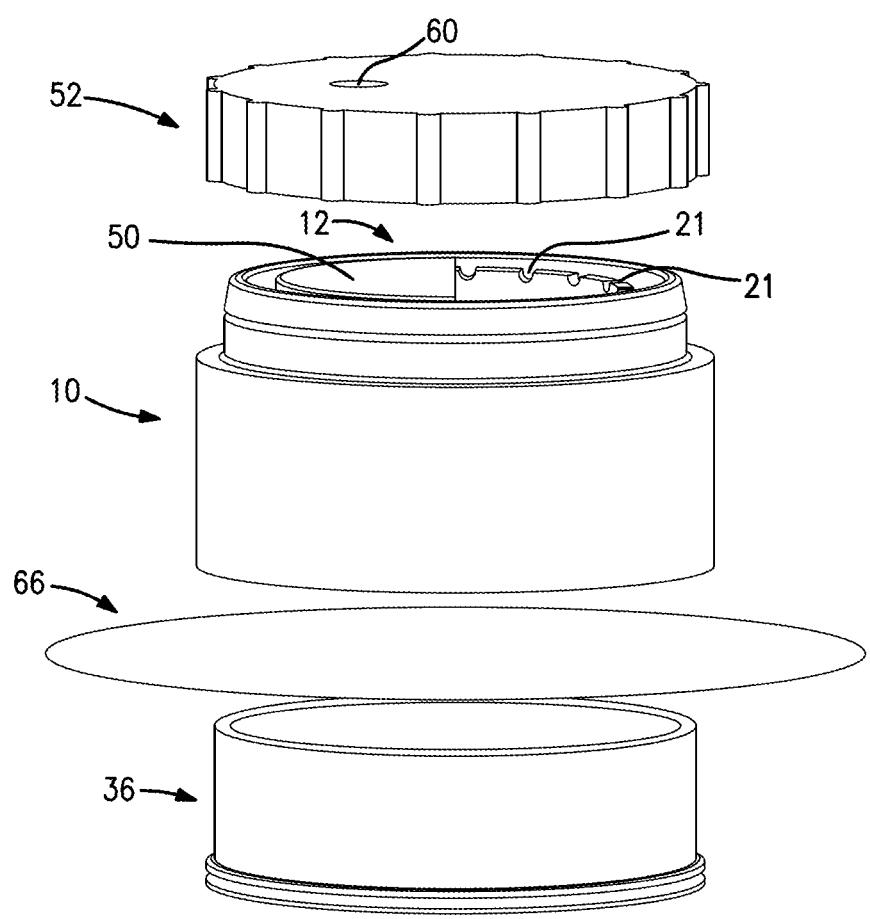
FIG. 4 is a top plan view of a cell body according to an aspect of the invention.

Referring still to FIG. 1, a cap 52 configured for assembling with the cell body 10 includes a top surface 54, a bottom surface 56, and a peripheral sidewall 58 that extends downwardly from the top surface 54 of the cap 52. The cap 52 includes a vent or through-hole 60 that extends from the top surface 54 through to the bottom surface 56. The vent hole 60 is off-centered, as illustrated in FIG. 1. The cap 52 may also include an internal annular bead or projection 64 disposed on the inner surface 65 of the peripheral sidewall 58. A top plan view of the cap 52 illustrating the planar member 50 and the series of channels 21 is illustrated in FIG. 4.

The diameter of vent hole 60 is a factor to consider with respect to the rate of withdrawal of any contained air or gases to be evacuated when attempting to reach equilibrium of pressure from within an assembled sample cup 100 and the sample analysis chamber of the instrumentation. Attaining equilibrium of pressure is necessary, for example, when a sample substance is in a fine, powdered form, and having a low density. The powdered sample tends to become airborne during the initial evacuation surge. With the advantage of independent user control of the vent, this condition is eliminated, since a greater volume of any entrapped air or gas is evacuated with no or minimum disruptive effect to the sample substance particles.

When an assembled sample cup is used in a positive pressure environment, for example, an inert gas including helium being introduced into the sample chamber, the vent hole 60 serves as a point of entry for the inert gas into the sample chamber. By controlling the vent size, the rate of entry is also advantageously controlled by the user to maintain a planar sample plane and avert distension. Liquid samples behave in a similar manner, in that the initial surge of evacuation tends to agitate the liquid, which problem is avoided with the adjustable and moveable vent hole 60. A suitable vent hole diameter may range between about 0.175" (4.45 mm), although other suitable diameters may also be employed.

When a bead 64 is present on the cap 52, as further illustrated in FIGS. 2 and 3, the outer surface 23 of outer top wall 14 of cell body 10 includes a corresponding recess 62 configured for receiving the cap 52 in a snap-fit and rotational engagement. When a cap 52 with a bead 64 is disposed on the cell body 10 with a corresponding recess 62, the cap 52 may be rotated about the periphery of the cell body 10. In addition, the upper surface 35 of outer transverse horizontal wall 34 acts as a stop for the cap 52.

Figure 5:
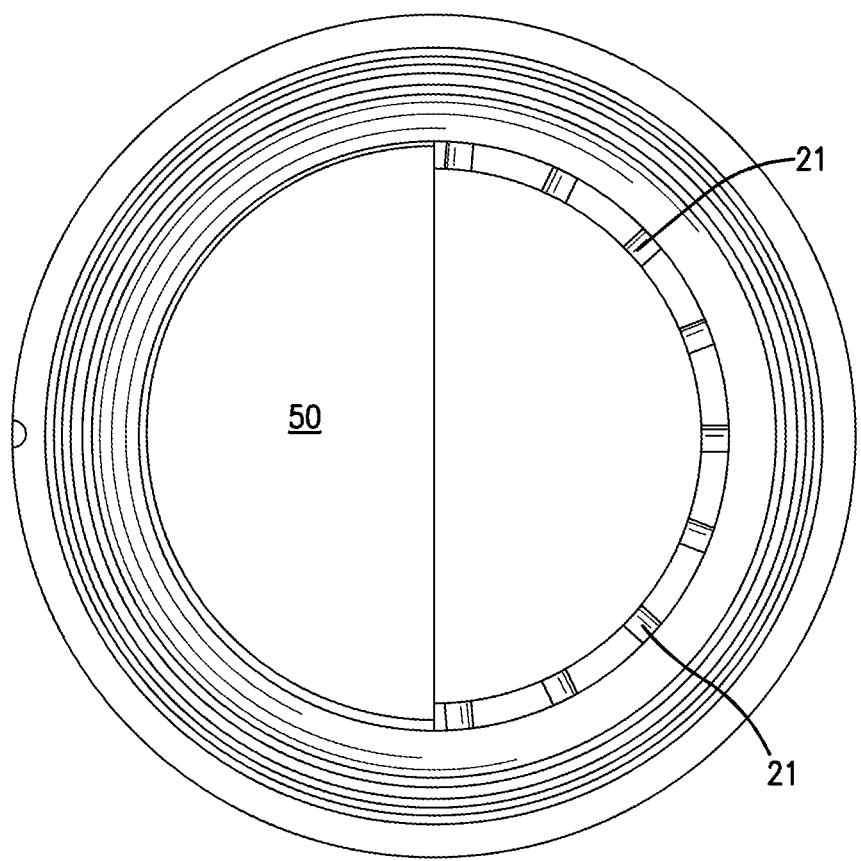
FIG. 5 is an exploded view of a sample cup according to an aspect of the invention.
Figure 6:
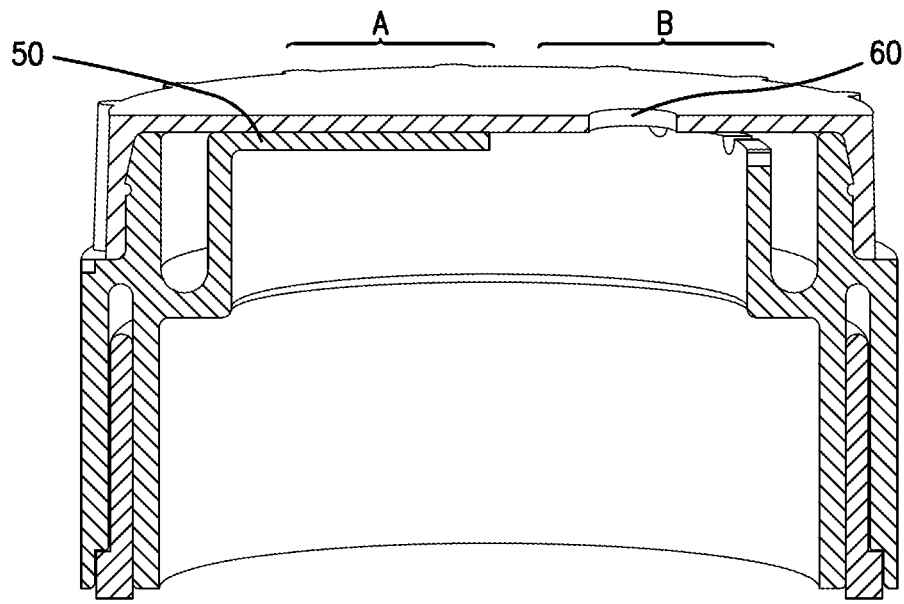
FIG. 6 is a cross-sectional view of a sample cup illustrating the vent hole in a closed position.
Figure 7:
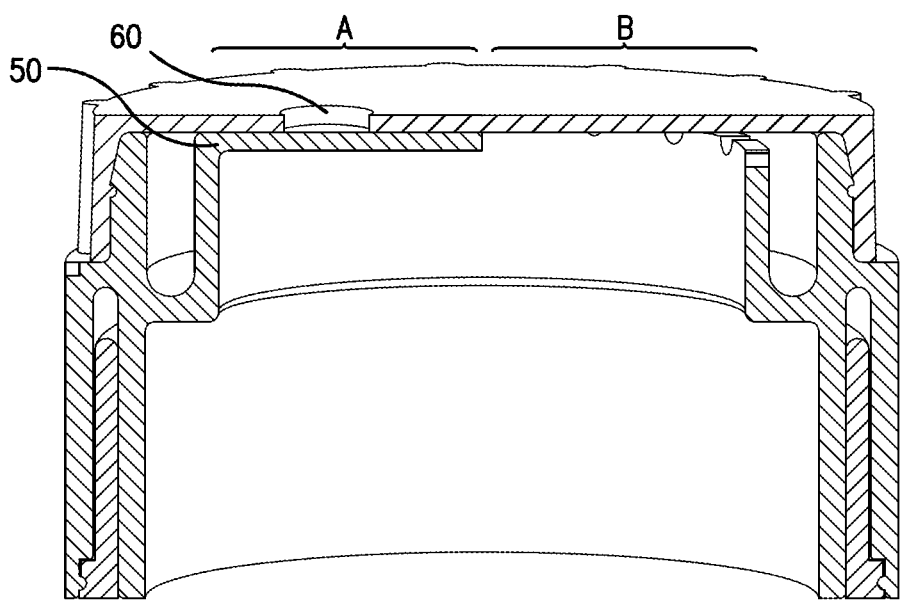
FIG. 7 is a cross-sectional view of a sample cup illustrating the vent hole in an open, vented position.

As further illustrated in FIG. 5, the cell body 10 includes a semi-circular disk-shaped planar member 50 that covers about one-half of the open top end 12. Rotation of cap 52 allows one to position the vent hole 60 directly over the open half A of the open top end 12, as illustrated in FIG. 6, to achieve maximum pressure equilibrium between the interior of the cup and the sample analysis chamber 27. The rate of equilibrium may also be controlled to maintain the thin film material 66 in a flat plane by rotating the cap 52 and positioning the vent hole 60 over the closed half B of the open top end 12, as illustrated in FIG. 7. Although a semi-circular member 50 is illustrated, it should be understood that alternative geometric shapes for member 50 may also be suitable.

As an additional advantage, after analysis is complete, the vent hole 60 may be repositioned over the semi-circular member 50 and sent to storage, which avoids contamination issues during the storage thereof, and maintains the specimen for future referral.

Assembling the sample cup and mounting a thin film of material across the open bottom end 26 according to an aspect of the invention includes providing a cell body 10, disposing a thin film of material 66 across the open bottom end 26, and inserting the annular collar 36 into the internal receiving channel 32. The annular collar 36 initially grasps the thin film of material 66 and is progressively advanced while drawing the thin film across the open bottom end 26 of the cell body 10, until the film material 66 is completely encased within the internal receiving channel 32, resulting in a taut, flat sample plane. A sample intended for analysis is disposed in the cell body 10 through the open top end 12. Thereafter, a rotatable cap may be disposed onto the top end 12 of the cell body, and placed in an analysis chamber of suitable instrumentation.

Referring to FIGS. 2 and 3, assembled sample cups according to various aspects of the invention are illustrated. Advantageously, upon assembly of the sample cup 100, the flanges 44 (FIG. 2) and 44' (FIG. 3), which assist in handling the cup upon assembly, are embedded within the corresponding recesses 46 and 46' of the cell body 10 to help maintain a taut, flat plane for precise and accurate analysis.

The cell body 10, the annular collar 36 and cap 52 may be formed of an appropriate polymer, for example, polyethylene. The thin film of material 66 may be formed from polyethylene, polyester, polyethylene terephthalate, polypropylene, polyimide, polycarbonate, ETNOM, or other materials exhibiting minimal and comparative absorption that are suitable for spectroscopic analysis. The ETNOM brand of thin film material, along with the others described above, are available from Chemplex Industries, Inc.

Advantageously, by using a suitably-sized thin film of material 66, the thin film of material 66 will be completely encased within the internal receiving channel 32 of the cell body 10, thus avoiding the need to trim or contend with clippings that tend to cling to surfaces. As an additional advantage, the assembled sample cup includes smooth outer surfaces, without any potentially interfering projections that can impede introduction, retention or removal from an analysis chamber.

The invention has been described with reference to specific embodiments. One of ordinary skill in the art, however, appreciates that various modifications and changes can be made without departing from the scope of the invention as set forth in the claims. For example, although the cell body and annular collar are illustrated as being flush, the annular collar may protrude or extend outwardly from the cell body, as in FIG. 6. Accordingly, the specification is to be regarded in an illustrative manner, rather than with a restrictive view, and all such modifications are intended to be included within the scope of the invention.

It should be understood that the aforementioned descriptions with respect to the upper and lower, and inner and outer elements of the cell, for example, are merely for convenience, and are not intended to be limiting.

Benefits, other advantages, and solutions to problems have been described above with regard to specific embodiments. The benefits, advantages, and solutions to problems, and any element(s) that may cause any benefits, advantages, or solutions to occur or become more pronounced, are not to be construed as a critical, required, or an essential feature or element of any or all of the claims.

What is claimed is:

1. A sample analysis cup, comprising:
   a cell body comprising:
   an open top end including an outer top wall and an inner top wall with an inner top edge, each of said walls extending axially and positioned in concentric relationship;
   a bottom wall extending from said outer top wall to said inner top wall, said bottom wall and said inner and outer top walls defining an internal reservoir therebetween;
   a planar member extending a selected distance from said inner top edge of said inner top wall, said planar member partially closing said open top end;
   an open bottom end including an outer bottom wall and an inner bottom wall, each of said walls extending axially and positioned in concentric relationship, said outer and inner bottom walls defining an internal channel therebetween; and
   a hollow chamber defined between said open top end and said open bottom end.

2. The sample cup according to claim 1, further comprising:
   a rotatable cap, comprising:
   a top surface;
   a bottom surface;
   a peripheral sidewall extending downwardly from said bottom surface of said cap; and
   an aperture extending from said top surface to said bottom surface.

3. The sample cup according to claim 2, wherein said aperture is off-centered.

4. The sample cup according to claim 1, further comprising an annular ring member being configured for insertion into said internal channel.

5. The sample cup according to claim 4, wherein said annular ring member includes an open top end and an open bottom end, and a substantially cylindrical wall.

6. The sample cup according to claim 5, wherein said annular ring member includes an external peripheral flange disposed about said open bottom end, and said outer bottom wall of said cell body includes an internal peripheral recess having a shape complementary to said external peripheral flange.

7. The sample cup according to claim 5, wherein said annular ring member further includes an external peripheral flange with a bead and indent cross-section disposed about said open bottom end, and said outer bottom wall of said cell body includes an internal peripheral recess having a shape complementary to said bead and indent cross-section.

8. The sample cup according to claim 2, wherein said outer top wall of said cell body includes an annular recess, and an inner surface of said sidewall of said cap includes an annular projection for engaging with said annular recess.

9. The sample cup according to claim 1, further comprising a thin film of material.

10. The sample cup assembly according to claim 9, wherein said thin film of material comprises a polymer.

11. The sample cup according to claim 1, wherein said outer top wall of said cell body includes an outer top edge, and said inner top wall includes an inner top edge, each of said edges being in the same plane.

12. The sample cup according to claim 1, wherein said outer top wall of said cell body includes an outer top edge, and said inner top wall includes an inner top edge, said inner top edge being disposed a selected distance below said outer top edge.

13. A sample cup assembly, comprising:
   a cell body, comprising:
   an open top end including an outer top wall and an inner top wall with an inner top edge, each of said top walls extending axially and positioned in concentric relationship;
   a bottom wall extending from said outer top wall to said inner top wall, said bottom wall and said inner and outer walls defining an internal reservoir therebetween;
   a planar member extending a selected distance from said inner top edge of said inner top wall, said planar member partially closing said open top end;
   an open bottom end including an outer bottom wall and an inner bottom wall, each of said bottom walls extending axially and positioned in concentric relationship, said outer and inner bottom walls defining an internal channel therebetween; and
   a hollow analysis chamber defined between said open top end and said open bottom end;
   a thin film of material;
   an annular ring member configured for insertion into said internal channel for retaining said thin film of material; and
   a rotatable cap configured for placement on said open top end.

14. The sample cup assembly according to claim 13, wherein said rotatable cap comprises:
   a top surface;
   a bottom surface;
   a peripheral sidewall extending downwardly from said bottom surface of said cap; and
   an aperture extending from said top surface to said bottom surface.

15. The sample cup assembly according to claim 14, wherein said aperture is off-centered.

16. The sample cup assembly according to claim 13, wherein said annular ring member includes an external peripheral flange disposed about said open bottom end, and said outer bottom wall of said cell body includes an internal peripheral recess having a shape complementary to said external peripheral flange.

17. A method for mounting a thin film of material across an open end of a sample analysis cup, comprising the steps of:
   providing a cell body comprising:
   an open top end including an outer top wall and an inner top wall with an inner top edge, each of said top walls extending axially and positioned in concentric relationship;
   a bottom wall extending from said outer top wall to said inner top wall, said bottom wall and said outer and inner top walls defining an internal reservoir therebetween;
   a planar member extending a selected distance from said inner top edge of said inner top wall, said planar member partially closing said open top end;
   an open bottom end including an outer bottom wall and an inner bottom wall, each of said bottom walls extending axially and positioned in concentric relationship, said outer and inner bottom walls defining an internal channel therebetween; and a hollow chamber defined between said open top end and said open bottom end;

disposing a thin film of material across said open bottom end;

inserting an annular ring member into said internal channel; and disposing a rotatable cap on said partially closed open top end.

18. The method according to claim 17, wherein the step of disposing a rotatable cap further comprises:

providing a rotatable cap, comprising:

a top surface;

a bottom surface;

a peripheral sidewall extending downwardly from said bottom surface of said cap; and an off-set aperture extending from said top surface to said bottom surface.

19. The method according to claim 18, further comprising the step of:

rotating the cap to place the off-set aperture over the open top end of said cell body.

20. The method according to claim 18, further comprising the step of:

rotating the cap to place the off-set aperture over the partially closed open top end of said cell body.

\* \* \* \* \*